United States Patent [19]
Alpern et al.

[11] Patent Number: 6,029,805
[45] Date of Patent: Feb. 29, 2000

[54] MULTIPLE SUTURE RETAINER AND SUTURE PACKAGE

[75] Inventors: Marvin Alpern, Glen Ridge; Michael Stephen Pohle, Flemington, both of N.J.

[73] Assignee: Ethicon, Inc., Somerville, N.J.

[21] Appl. No.: 09/218,317

[22] Filed: Dec. 22, 1998

[51] Int. Cl.⁷ .................................................. A61B 17/04
[52] U.S. Cl. .......................... 206/63.3; 206/227; 206/388
[58] Field of Search .................................. 206/63.3, 227, 206/380, 382, 388

[56] References Cited

U.S. PATENT DOCUMENTS

| | | | |
|---|---|---|---|
| 3,444,994 | 5/1969 | Kaepernik et al. | 206/63.3 |
| 4,483,437 | 11/1984 | Cerwin et al. | 206/63.3 |
| 5,101,968 | 4/1992 | Henderson et al. | 206/63.3 |
| 5,121,836 | 6/1992 | Brown et al. | 206/63.3 |
| 5,566,821 | 10/1996 | Brown et al. | 206/63.3 |
| 5,584,164 | 12/1996 | Sinn | 206/63.3 X |
| 5,746,311 | 5/1998 | Brown et al. | 206/63.3 |

Primary Examiner—Bryon P. Gehman

[57] ABSTRACT

A suture package comprising a needled suture or a non-needled suture, in the same folding retainer. The retainer comprises first and second suture-supporting panels hinged together along a common side edge; a cover panel hinged to each of the supporting panels along a common side edge; and a closing mechanism for releasably closing the panels together, folded about the hinges to retain a suture; one of the supporting panels and one of the cover panels including two separate access features providing access to either a needled or non-needled suture.

7 Claims, 11 Drawing Sheets

MULTIPLE SUTURE RETAINER AND SUTURE PACKAGE

FIELD OF THE INVENTION

This invention relates to packages of surgical sutures, and particularly to a retainer in such a package that can releasably retain either a needled suture or a non-needled suture in the same package.

BACKGROUND OF THE INVENTION

The prior art is replete with examples of a variety of paper suture retainers that fold up to releasably retain either a needled suture or a non-needled suture as a package. Commonly, two suture-supporting panels are hinged together and each to a cover panel, as in, for example, U.S. Pat. No. 4,249,656. In the latter example, an openable perforation 20 is provided that allows access to a needled suture. In other, different retainers, a non-needled suture has been retained.

Some suture package examples include interlocking slits at one end of the panels to act as closure tabs to keep the package closed, as shown for example in U.S. Pat. No. 5,746,311 (slits 112, 122, 132, and 142).

Although such suture retainers have functioned more or less as intended, different retainers are required to provide a needled suture and a non-needled suture. No single paper-based retainer or package has sufficed to accommodate either a needled—or a non-needled suture with easy accessibility.

Additionally, non-needled suture retainers have provided access to the suture only with some difficulty.

Accordingly, prior to this invention there has been a need to provide a suture retainer suitable for mounting either kind of suture within the same package, and particularly, one that provides easy accessibility to the suture.

SUMMARY OF THE INVENTION

I have constructed a suture retainer and package that meets the aforesaid need.

More particularly, in accord with one aspect of the invention, there is provided a suture package comprising, in combination, a folded retainer and at least a non-needled suture, the suture including a grasping tab thereon; the retainer comprising four adjacent panels each hingedly attached to an adjacent panel, two of the panels comprising a cover panel and two of the panels comprising a suture supporting panel, the suture being foldably positioned in contact with the support panels; one of the cover panels including means defining a slit therein, the grasping tab being positioned to an extent partway through the cover for operator access; the cover panels being each folded over a portion of the suture and one of the support panels to keep the suture from unraveling.

In accord with another aspect of the invention, there is provided a multi-purpose folding retainer for either a needled suture or a non-needled suture, the retainer comprising: first and second suture-supporting panels hinged together along a common side edge; a cover panel hinged to each of the supporting panels along a common side edge; and closing means for releasably closing the panels together, folded about the hinges to retain a suture; one of the supporting panels and one of the cover panels including two separate means defining access to either a needled suture or a non-needled suture between the panels.

In accord with yet another aspect of the invention, there is provided such a retainer wherein the closing means comprises a closure tab on one of the panels and a mating slot for the tab on another of the panels, the closure tab and slot when mated being effective to hold the panels folded together with a suture inside; and the two separate access-defining means comprise, in one of the panels, a slit for a grasping tab on a non-needled suture, and in the other, an openable perforation for a needled suture.

In accord with still another aspect of the invention, there is provided a suture package comprising a folding retainer as noted above, with either a needled suture or a non-needled suture retained therein.

Accordingly, it is an advantageous feature of the invention that the same single folding suture retainer can be used with either a needled or a non-needled suture, and still provide easy accessibility of the suture.

DETAILED DESCRIPTION OF THE INVENTION

The invention is described in connection with certain preferred embodiments, in which a retainer of the package comprises four panels of particular shape and size hinged together at particular locations thereon, for folding in a particular sequence to enclose as part of the package, a needled or non-needled suture of a particular type, the panels including preferred slits and perforations, and interlocking structure of a particular type to removably lock the retainer in its closed configuration. In addition, the invention is useful to provide a retainer and package regardless of the number, shape or size of the panels of the retainer, regardless of the locations of the hinges connecting the panels, regardless of the sequence of assembly or the type of sutures packed therein, regardless of the location, shape or size of slits and perforations, and regardless of the interlocking structure used to keep the package closed temporarily.

Figure 1:
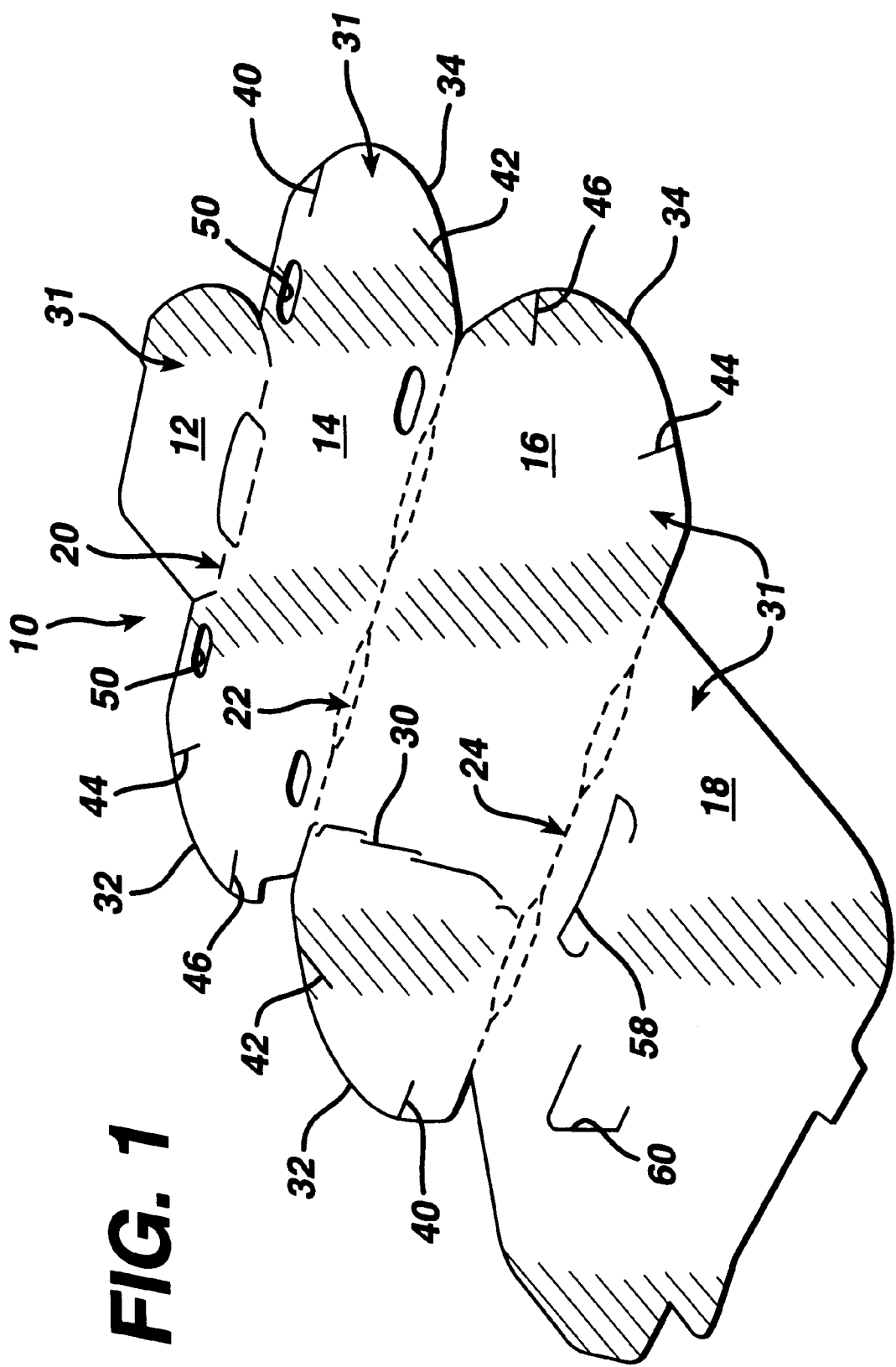
FIG. 1 is a perspective view of a suture-containing folding retainer constructed in accordance with the invention, but without the suture and prior to folding.
Figure 2:
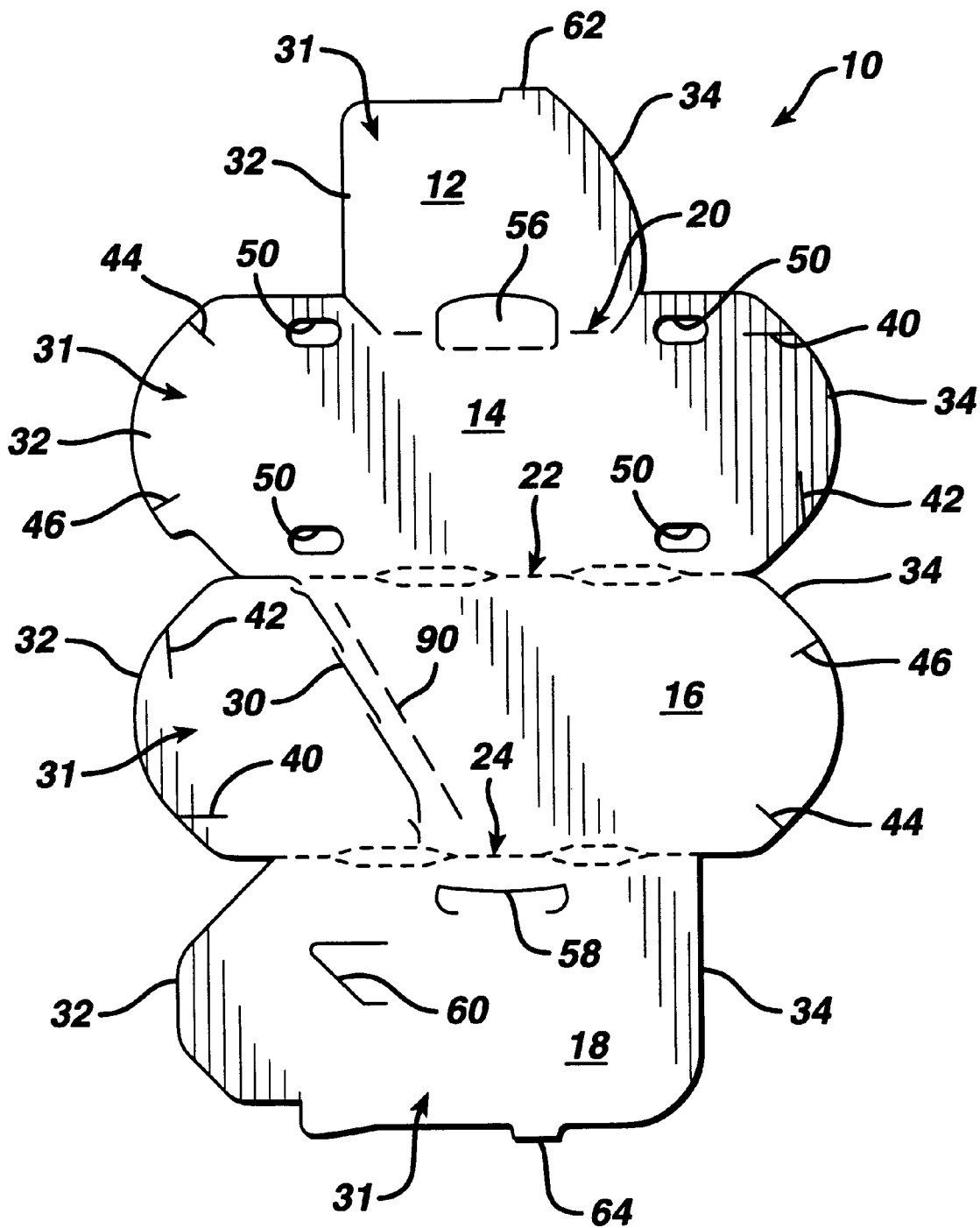
FIG. 2 is a plan view of the retainer of FIG. 1.

Turning next to FIGS. 1 and 2, the folding retainer 10 for sutures of the invention comprises, as is conventional, four adjacent panels 12, 14, 16, and 18 hinged together in sequence at 20, 22, and 24. A similar structure is shown in FIG. 1 of said '656 patent. Panels 14 and 16 are supporting panels for the suture to be packaged within, and panels 12 and 18 are cover panels for their respective adjacent suture-supporting panels, as will become apparent. A perforation 30 is also conventionally included in supporting panel 16, to allow a needle of a needled suture to be accessed. Surfaces 31 are the inside surfaces of the panels.

Each panel has opposing ends 32, 34, and in those ends of panels 14 and 16, at least one and preferably two slits 40, 42 or 44, 46 are formed, as shown. Slits 40 are generally and preferably straight and aligned with hinge lines 22, 24 and preferably angled at about 45° with slits 44, and slits 42 and 46 are also preferably angled at about 45° with respect to each other. Similar slits, albeit one only at each panel end, are shown in, e.g., said '311 U.S. Patent, for the same interlocking purpose.

To provide access to the interior of the package for winding the sutures about posts, apertures 50, FIG. 2, are provided in panel 14, also as is conventional.

To releasably close retainer 10 after folding about hinges 22 and 24 (described hereinafter), a closure tab 56 is provided as an integral part of the panels, preferably in supporting panel 14, and a mating slot 58 is provided within another panel, preferably cover panel 18, aligned with tab 56.

In accordance with one aspect of the invention, a slit 60 is included in the panel 18, shaped and sized to accommodate a portion of a grasping tab of a non-needled suture, extending partway through the panel.

To assist in keeping cover panels 12 and 18 closed during the folding steps, tabs 62, 64 are formed as extensions on their cover panels, aligned with each other and of sufficient size as to abut each other during folding, described hereinafter.

One preferred assembly of the package is shown in FIGS. 3 through 6. That is, winding posts 70, 72 are disposed through apertures 50, FIG. 3, and if the retainer is to be for a needled suture, the needle 80 is placed across perforation 30 of suture-supporting panel 16, as shown. (The needle and suture are conventional and need no further description.)

Figure 4:
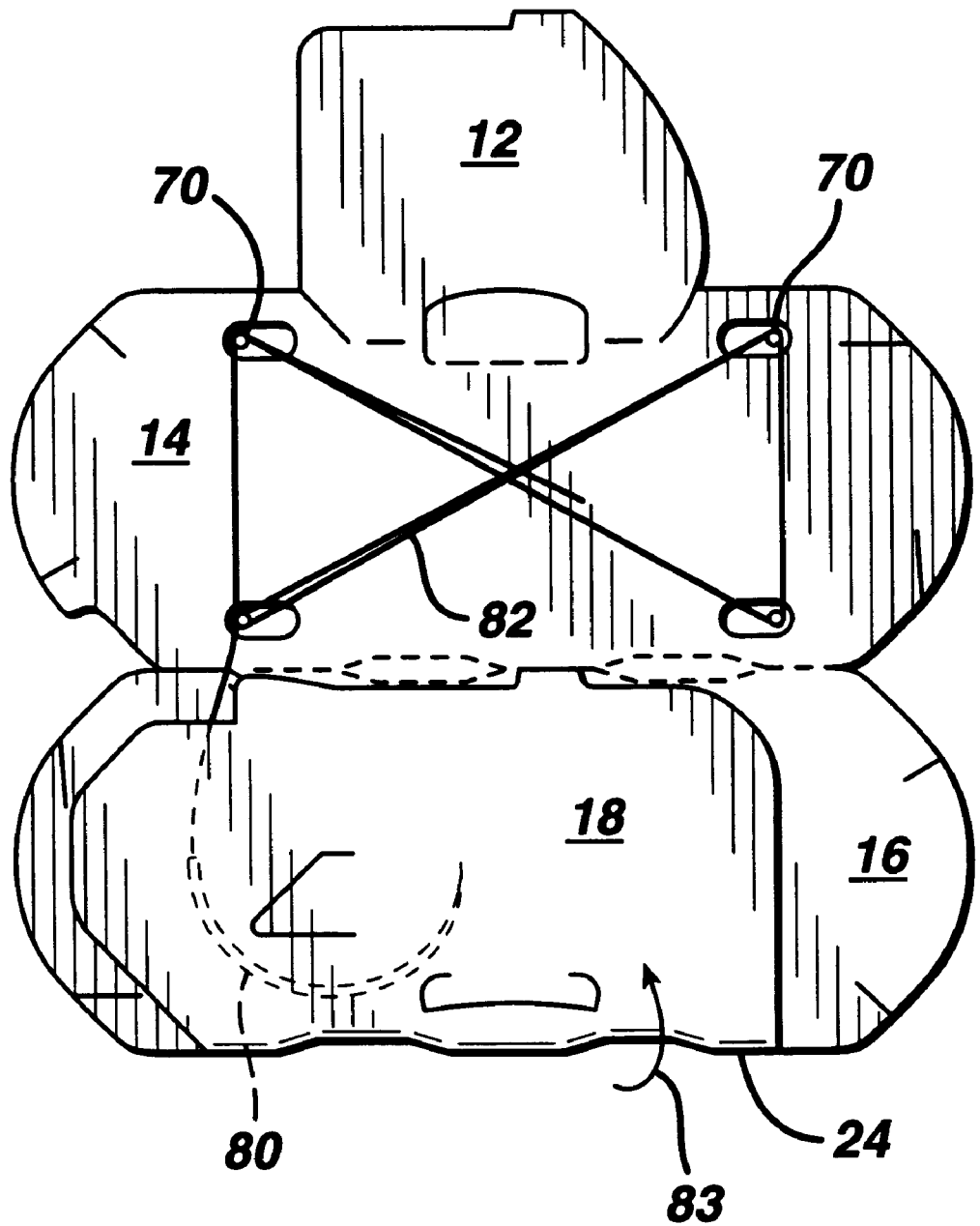
FIG. 4 is a plan view similar to that of FIG. 3, but with a needled suture wrapped on the other supporting panel and with a cover panel folded into position.
Figure 8:
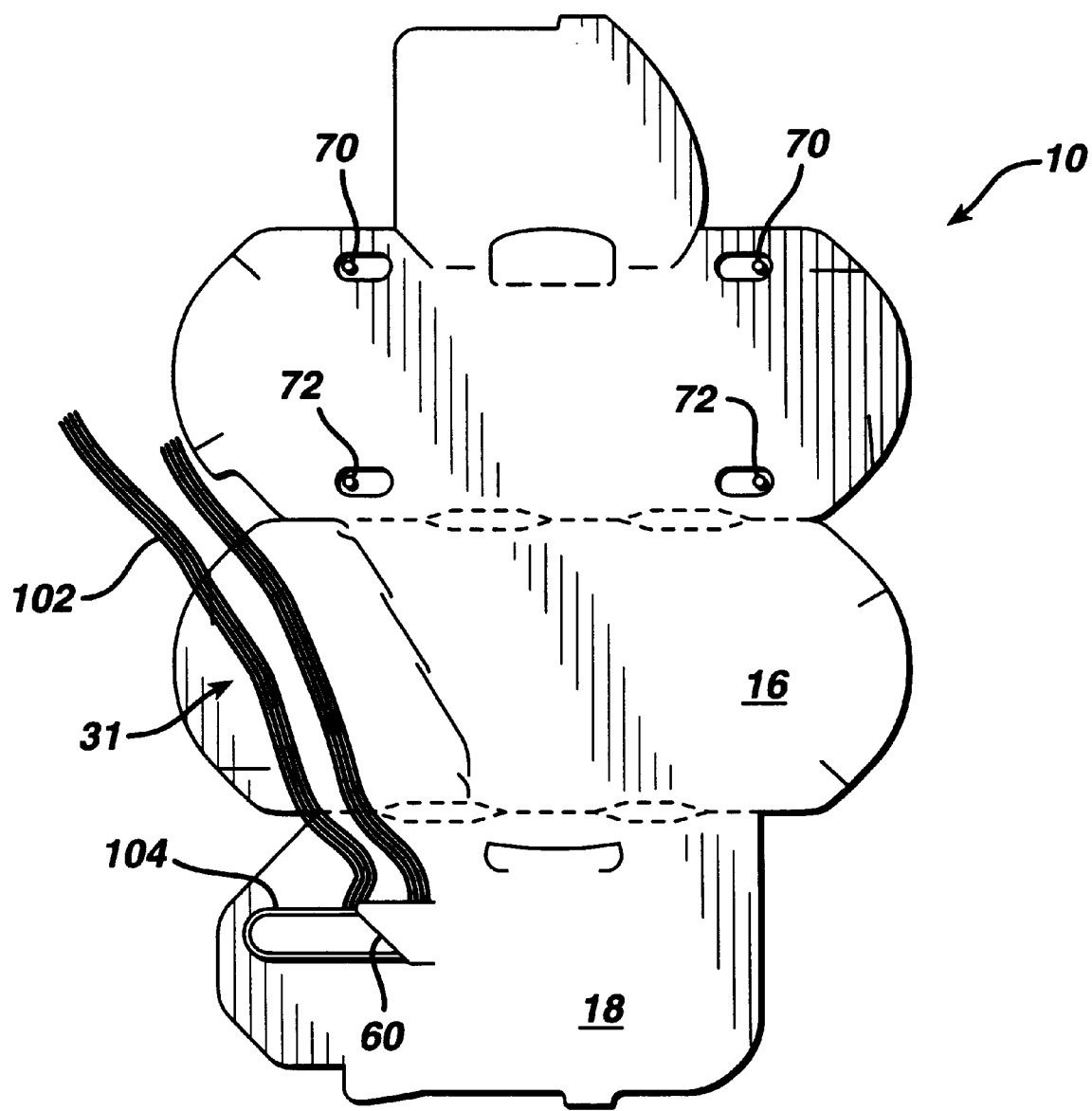
FIG. 8 is a plan view similar to that of FIG. 3, but using the non-needled suture of FIG. 7.

Next, FIG. 4, suture 82 attached to needle 80 is conventionally wrapped around posts 70, 72 in any desired pattern, a preferred one being a FIG. 8 as shown. (An oval pattern is another useful example.) Cover panel 18 is folded, arrow 83, about its hinge line so as to cover needle 80.

Figure 5:
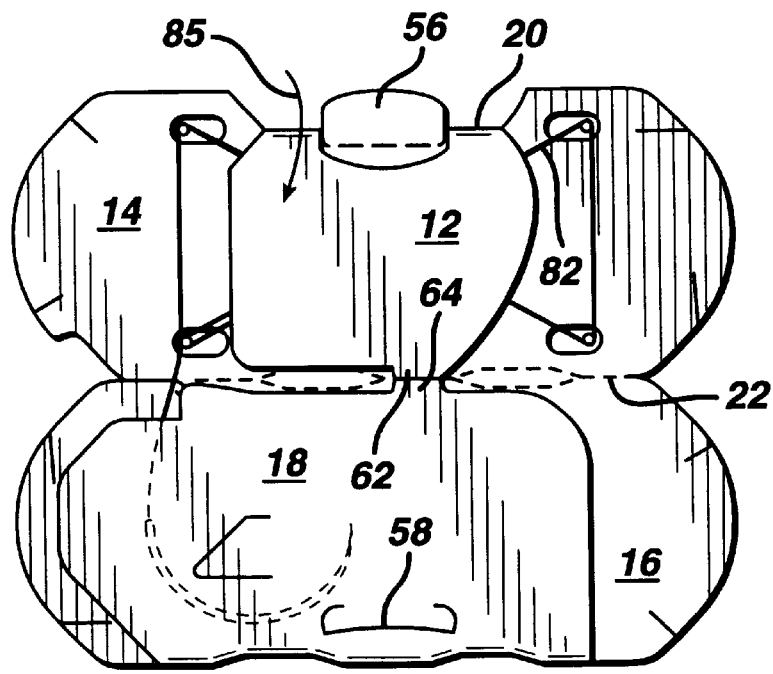
FIG. 5 is a plan view similar to that of FIG. 4, but with the other cover panel folded into position.

Next, FIG. 5, cover panel 12 is folded, arrow 85, about its hinge line 20, leaving closure tab 56 projecting, so that panel 12 covers the wound pattern of the suture 82, to keep it from unraveling.

Figure 6:
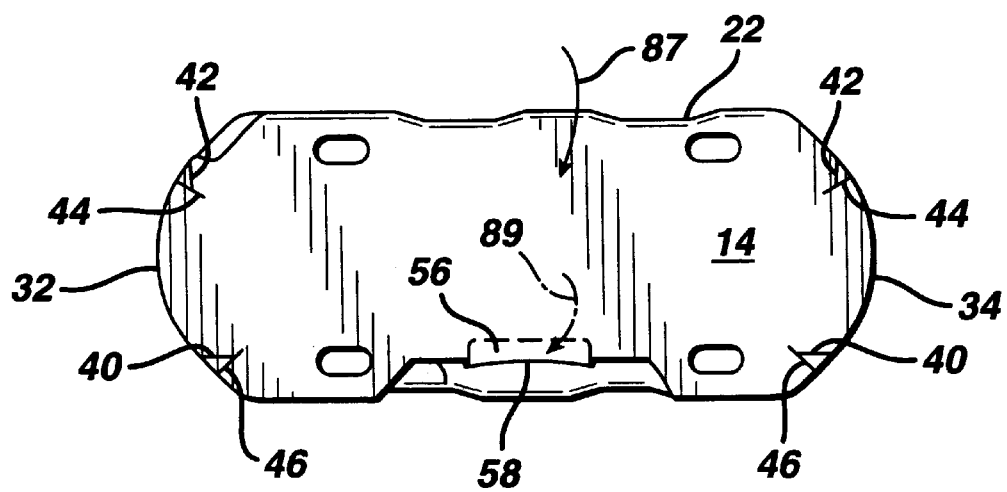
FIG. 6 is a plan view similar to that of FIG. 5, but with the two supporting panels folded into and engaged in the closed position of the package.
Figure 7:
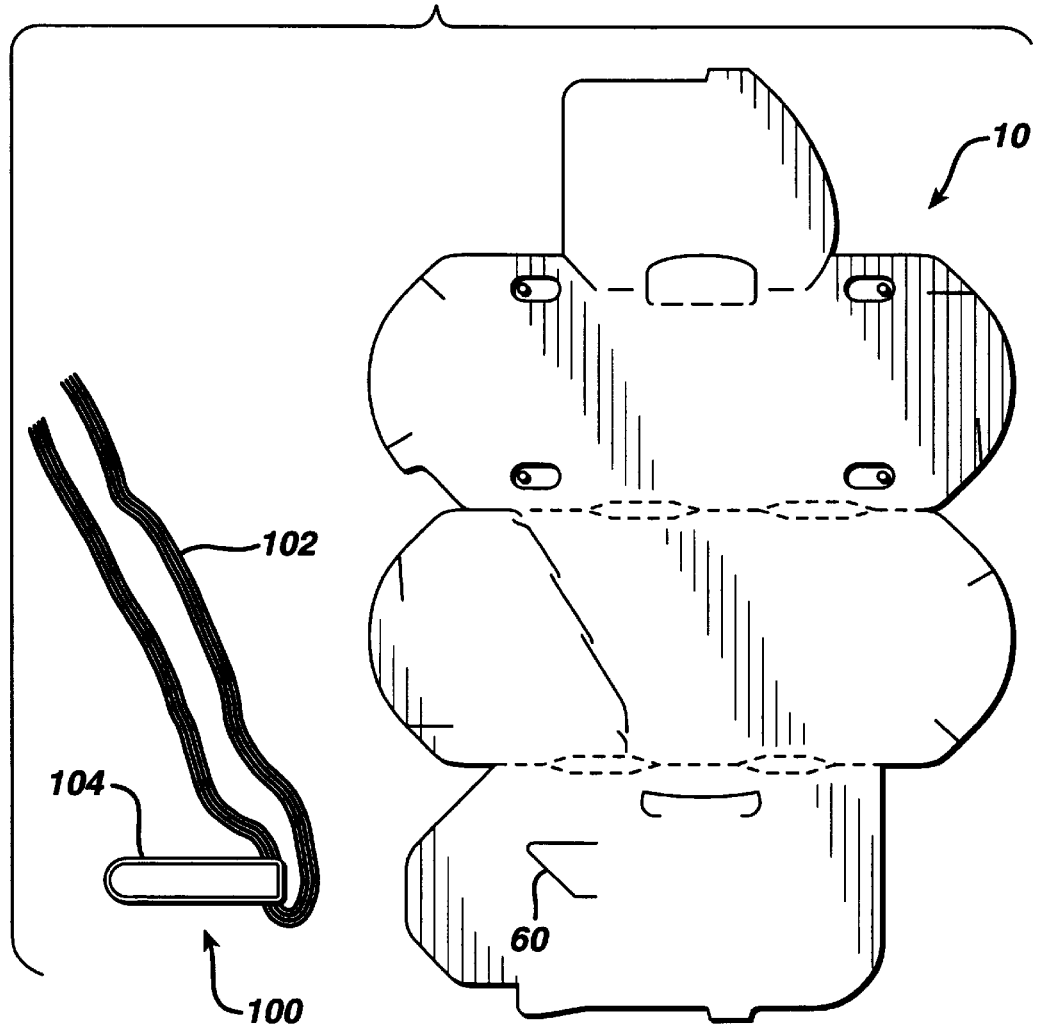
FIG. 7 is a plan view similar to that of FIG. 2 but showing the start of assembly of the package using a non-needled suture.
Figure 13:
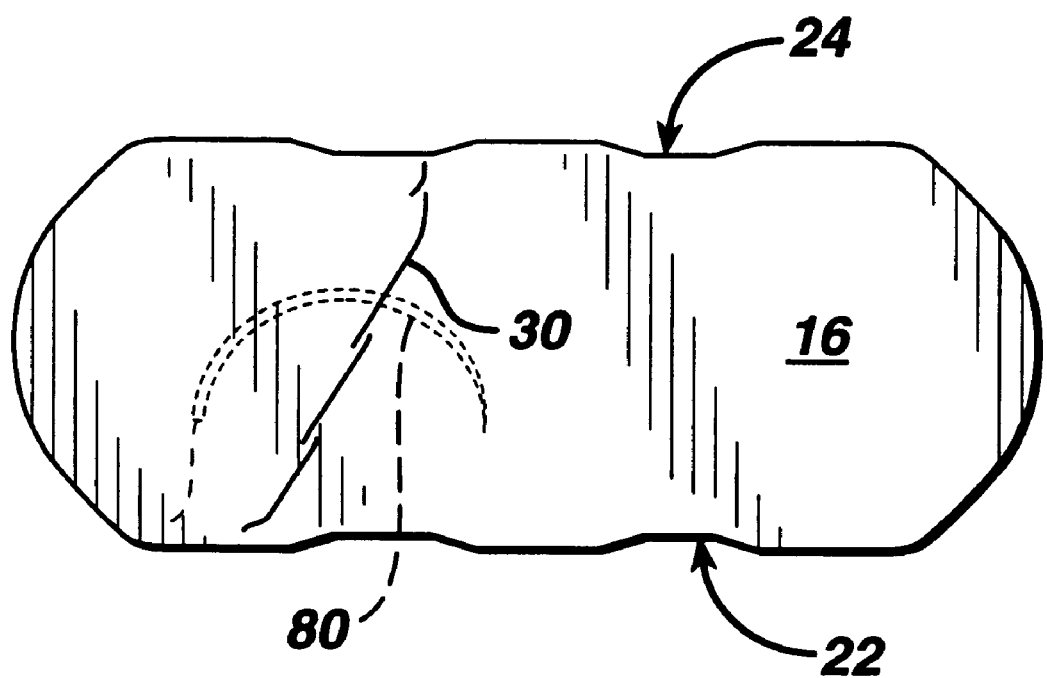
FIG. 13 is a plan view of the assembled package of FIG. 6, when viewed from the opposite side, showing the needled suture underlying its perforation.

Finally, FIG. 6, the two supporting panels 14 and 16 are folded, arrow 87, about their hinge line 22 so that cover panels 12 and 18 become adjacent to each other. The abutment of tabs, 62, 64, with each other, FIG. 5, assists in keeping cover panels 12 and 18 in contact with the suture and needle sandwiched between the cover and supporting panels, during this step. Tab 56 is inserted, arrow 89, into mating slot 58 for a releasable closure of the package, and paired slits 40, 44 and 42, 46 are twisted together, as is conventional, to releasably lock ends 32 of panels 14 and 16, and ends 34 of panels 14 and 16, together. The package is complete. As is apparent from FIG. 13, panel 16 provides at perforation 30, easy access to needle 80, simply by tearing open the perforation.

Figure 3:
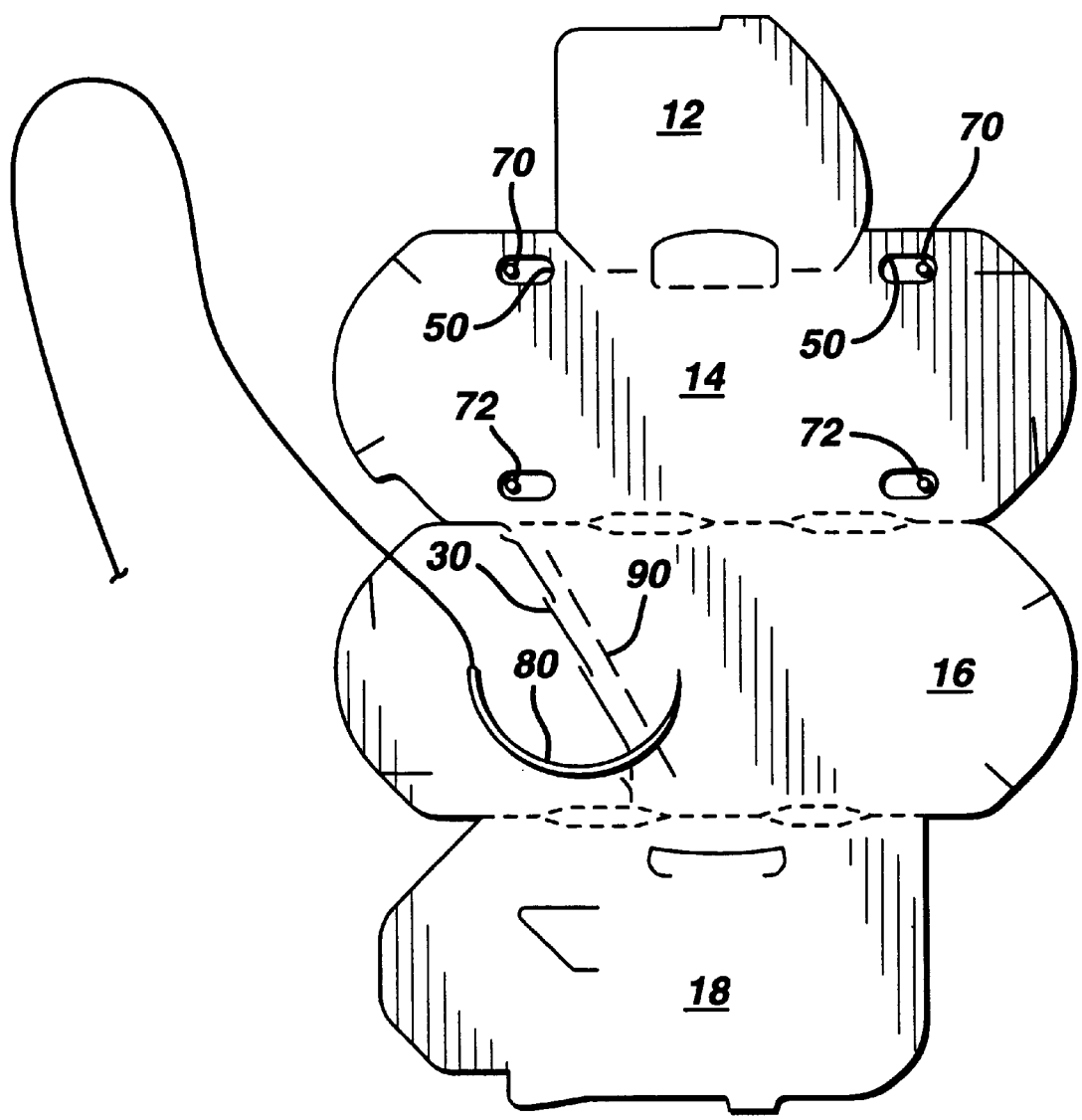
FIG. 3 is a plan view similar to that of FIG. 2, but with a needled suture positioned on its supporting panel as it appears in the assembly of the package comprising the retainer and suture.

Optionally (not shown), a needle park of conventional construction can be mounted on panel 16, adjacent to perforation 30 along the phantom line 90 shown in FIGS. 2 and 3, to further hold needle 80 in place, if desired.

In accordance with another aspect of the invention, the very same retainer 10 described in FIGS. 1 through 6, is useful, FIGS. 7 through 12, in packaging a non-needled suture 100 in place of the needled suture. Since the retainer 10 is itself identical to that described already, the same reference numerals are used for the retainer. The suture in this case comprises the threads 102 and a grasping tab 104, FIG. 7.

Hence, it is no longer necessary to provide a separate retainer for non-needled sutures, compared to that used for the needled ones.

To assemble, tab 104 is inserted part-way through slit 60 with the sutures resting on inside surface 31 of panel 16, FIG. 8. Winding posts 70, 72 are positioned as before.

Figure 9:
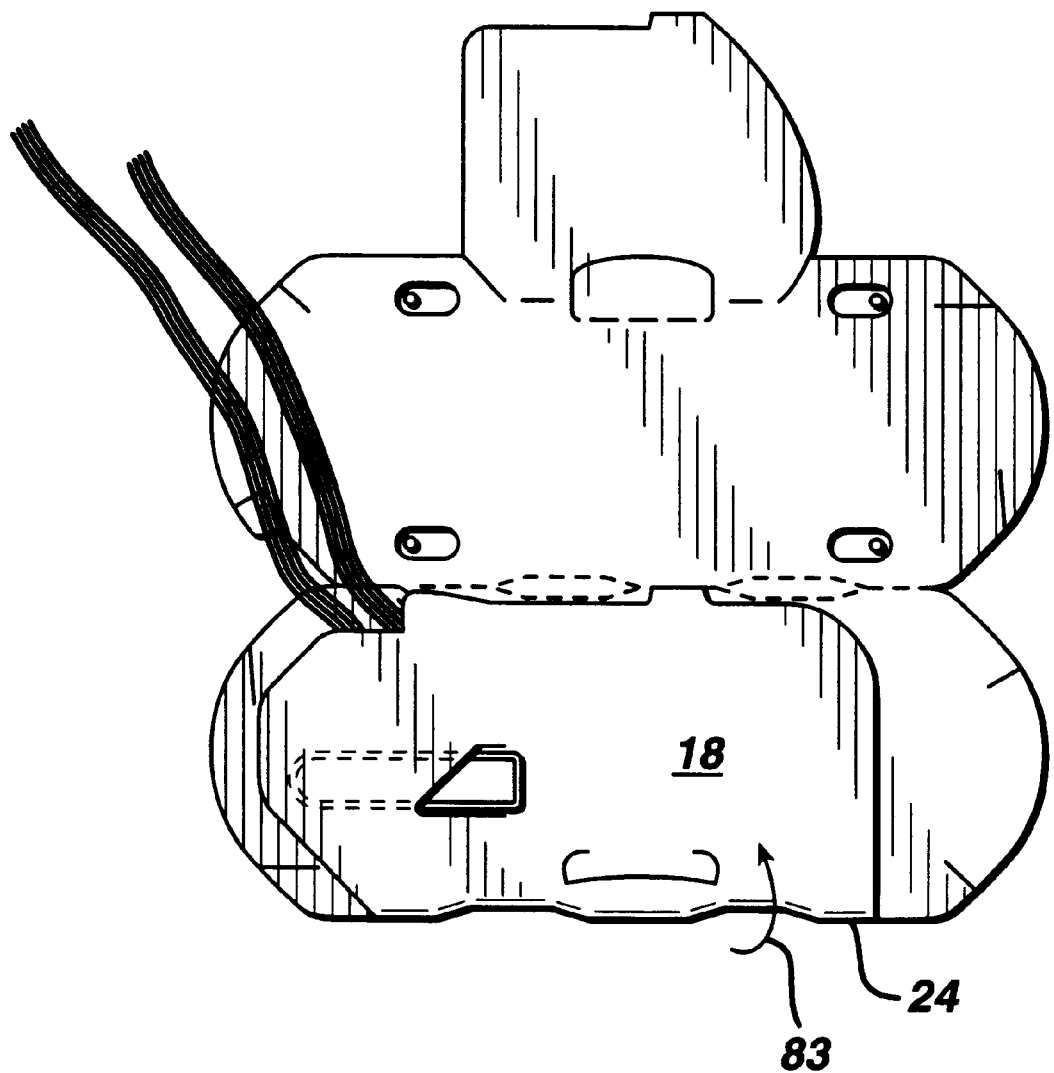
FIGS. 9 and 10 are plan views similar to that of FIG. 4, but showing wrapping and packaging of the non-needled suture.
Figure 10:
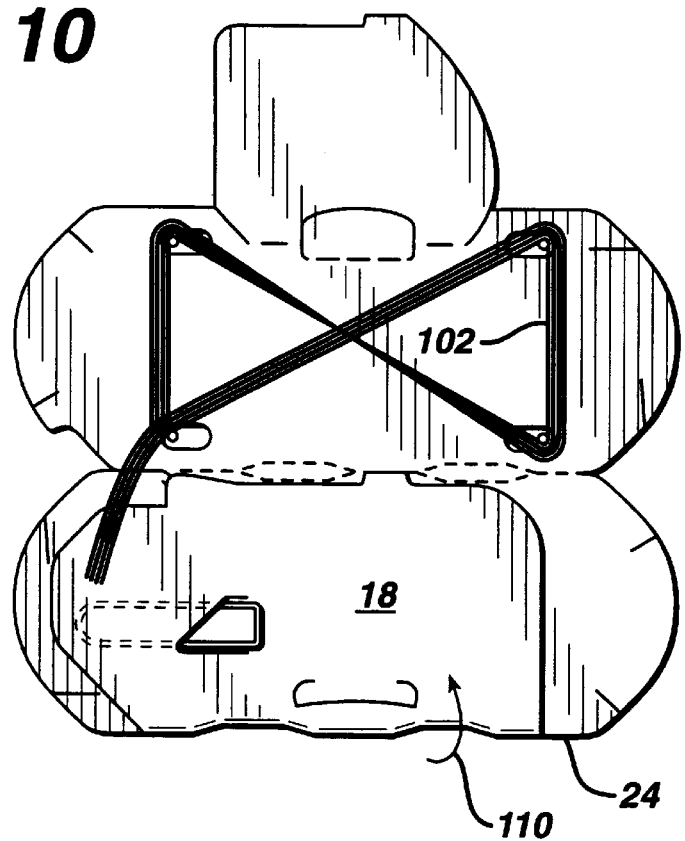

Next, FIG. 9, cover panel 18 is folded, arrow 83, about hinge line 24, and sutures 102 are wound about the winding posts in the preferred pattern, FIG. 10.

Figure 11:
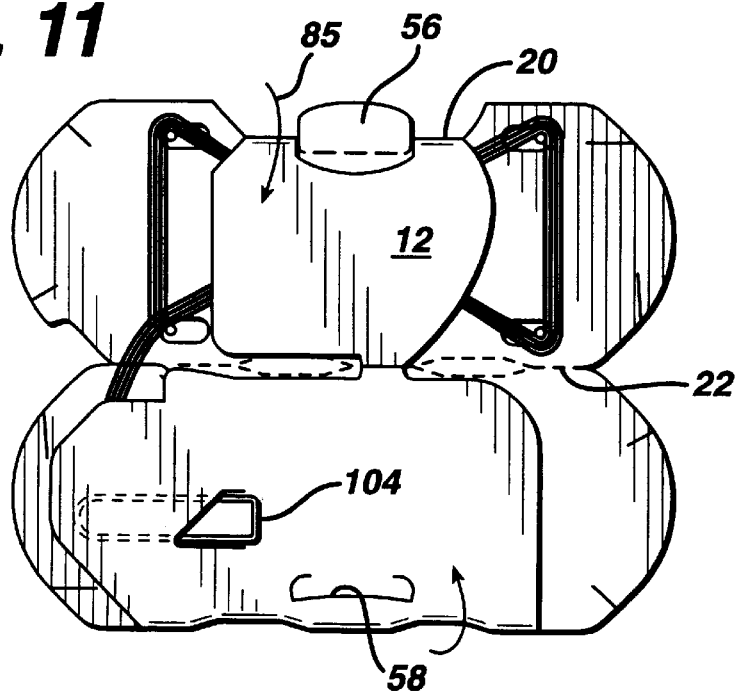
FIGS. 11 and 12 are plan views similar to that of FIGS. 5 and 6, respectively, but showing folding of the package as it contains the non-needled suture.
Figure 12:
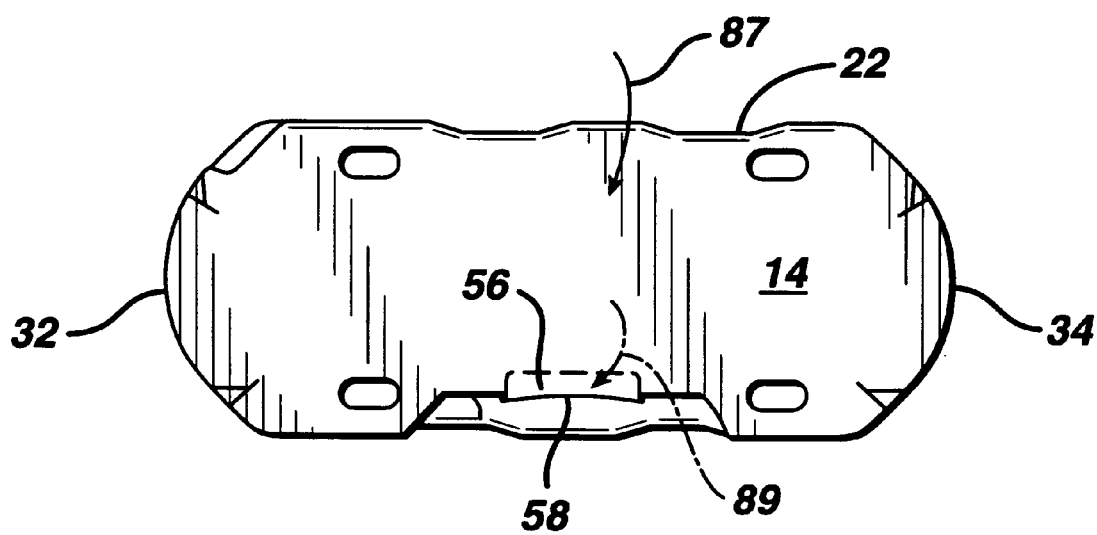

The remainder of the assembly process is the same as for the needled suture. FIG. 11, cover panel 12 is folded, arrow 85, about hinge line 20, and the two supporting panels are folded together, arrow 87, FIG. 12, about hinge line 22. Tab 56 is inserted into slot 58, arrow 89, and interlocking slits at ends 32, 34 are twisted into place.

It will be readily apparent, FIG. 11, that access to the non-needled suture requires only that tab 56 be pulled or released from slot 58 and the supporting panels pivoted about hinge line 22, so that the exposed portion of tab 104 can be grasped and pulled.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A suture package comprising, in combination, a folded retainer and at least a non-needled suture, said suture including a grasping tab thereon;

said retainer comprising four adjacent panels each hingedly attached to an adjacent panel, two of said panels each defining cover panels and two of said panels each defining suture supporting panels, said suture being foldably positioned in contact with said supporting panels;

one of said cover panels including means defining a slit therein, said grasping tab being positioned to an extent partway through said cover panels for operator access;

said cover panels being each folded over a portion of said suture and one of said support panels.

2. A package as defined in claim 1, wherein said supporting panels are hinged together at a common hinge and are folded together with said cover panels to create an interior space and said suture is contained within the space and the panels are in contact with each other, said supporting panels then being exposed; and further including a closure tab on at least one of said panels that releasable closes said package with said supporting panels folded together.

3. A package as defined in claim 2, wherein said closure tab is on one of said supporting panels, and further including in a cover panel not adjacent to said one supporting panel, means defining a mating slit into which said closure tab is inserted.

4. A package as defined in claim 2, wherein each of said panels has two opposite ends between which the panels are hingedly connected; and wherein said closure tab comprises interlocking slits in said supporting panels, said interlocking slits being located in at least one location at at least one of said ends.

5. A package as defined in claim 4, wherein said interlocking slits are located in two places at each of said opposite ends of each of said supporting panels.

6. A package as defined in claim 2, wherein one of said supporting panels further includes an operable perforation positioned so as to overlap said suture contained in the space within the package for easy removal by tearing open said perforation.

7. A package as defined in claim 1, wherein said suture is disposed between said supporting panels and said cover panels in a figure eight pattern.

* * * * *